United States Patent [19]

Kaplan et al.

[11] Patent Number: 4,482,720

[45] Date of Patent: Nov. 13, 1984

[54] CONTINUOUS PROCESS FOR PREPARING BENZOTHIAZYL DISULFIDE

[75] Inventors: Joel H. Kaplan, South Plainfield; Robert C. Kinstler, Somerville, both of N.J.

[73] Assignee: American Cyanamid Company, Stamford, Conn.

[21] Appl. No.: 342,318

[22] Filed: Jan. 25, 1982

Related U.S. Application Data

[63] Continuation of Ser. No. 758,222, Jan. 10, 1977, abandoned, which is a continuation-in-part of Ser. No. 640,583, Dec. 15, 1975, abandoned, which is a continuation of Ser. No. 461,036, Apr. 15, 1974, abandoned, which is a continuation of Ser. No. 230,079, Feb. 28, 1972, abandoned.

[51] Int. Cl.³ .......................................... C07D 513/00
[52] U.S. Cl. .................................... 548/158; 548/165
[58] Field of Search ........................ 548/158; 436/150

[56] References Cited

U.S. PATENT DOCUMENTS

| | | | |
|---|---|---|---|
| 2,385,410 | 9/1945 | Gardner | 548/158 |
| 2,468,952 | 5/1949 | Beber et al. | 548/158 |
| 3,062,825 | 11/1962 | Hardman et al. | 548/158 |

FOREIGN PATENT DOCUMENTS

2151260 4/1973 Fed. Rep. of Germany ...... 436/150

*Primary Examiner*—Glennon H. Hollrah
*Assistant Examiner*—D. B. Springer
*Attorney, Agent, or Firm*—Charles J. Fickey; Gordon L. Hart

[57] ABSTRACT

A continuous process for preparing benzothiazyl disulfide. More particularly, the invention relates to an improved continuous process for preparing benzothiazyl disulfide by oxidizing sodium mercaptobenzothiazole with chlorine under controlled conditions of pH, reactant concentrations, oxidation-reduction potential and agitation.

5 Claims, No Drawings

CONTINUOUS PROCESS FOR PREPARING BENZOTHIAZYL DISULFIDE

This is a continuation of application Ser. No. 758,222 filed Jan. 10, 1977 which was a continuation-in-part of application Ser. No. 640,583 filed Dec. 15, 1975 which was a continuation of application Ser. No. 461,036 filed Apr. 15, 1974 which was a continuation of application Ser. No. 230,079 filed Feb. 28, 1972, all of which are now abandoned.

Generally stated, the subject matter of the present invention relates to a continuous process for preparing benzothiazyl disulfide. More particularly, the invention relates to an improved continuous process for preparing benzothiazyl disulfide by oxidizing sodium mercaptobenzothiazole with chlorine under controlled conditions of pH, reactant concentrations, oxidation-reduction potential and agitation.

BACKGROUND OF THE INVENTION

An important conventional process for oxidizing 2-mercaptobenzothiazole to benzothiazyl disulfide uses chlorine gas as the oxidizing agent, the chlorine being dispersed into a stirred aqueous solution of the sodium salt of the 2-mercaptobenzothiazole. The oxidation reaction using chlorine would normally be expected to follow the overall stoichiometry of the reaction as shown below:

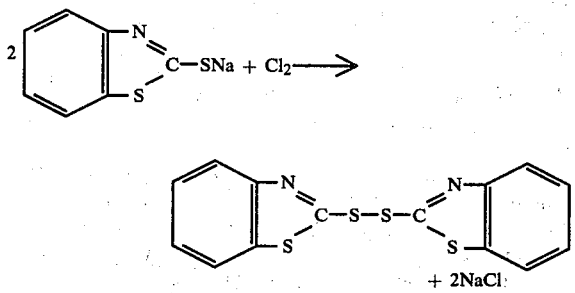

The reaction equation shows that ideally no acidic or basic substance should be formed to change the pH of the aqueous mixture as chlorine is used to oxidize a solution of the sodium salt of 2-mercaptobenzothiazole to benzothiazyl disulfide. However, in actual practice and as taught in prior art, it is necessary to add alkali solution to the reaction mixture as the chlorine is added or to have present before hand excess alkali in a buffer in order to prevent the mixture from becoming acidic and consequently forming benzothiazyl disulfide contaminated with free 2-mercaptobenzothiazole. The amount of alkali required to hold the pH constant or prevent its dropping below about pH 8.5–9.5 is often as much as 0.3 to 1.0 molecular equivalent per mole of 2-mercaptobenzothiazole (as taught, for example, in U.S. Pat. No. 2,468,952 to Adolph J. Beber).

A study of the by-products formed, and the reaction rates leading thereto, during oxidation of 2-mercaptobenzothiazole with chlorine in aqueous alkaline mixture explains why additional alkali is necessary. Several water soluble "over-oxidized" products, primarily sodium benzothiazyl-2-sulfinate (I) and sodium benzothiazyl-2-sulfonate (II) are formed along with the disulfide during the oxidation. The "over-oxidation" reactions require additional chlorine usage and form hydrochloric acid. The "over-oxidation" reactions are shown below:

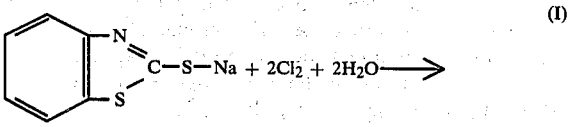

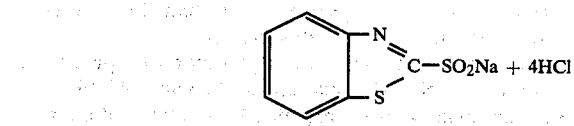

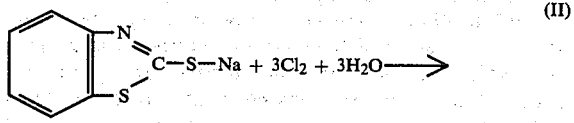

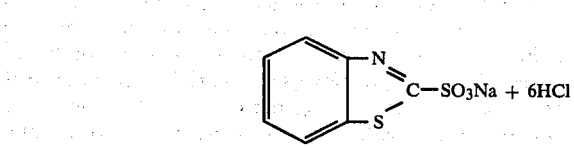

If no excess free alkali is added to the reaction mixture before or during chlorine addition, then the drop in pH occasioned by the formation of hydrochloric acid causes precipitation of free 2-mercaptobenzothiazole. The free thiol precipitates from its sodium salt at a pH below about 8.5 to 9.5. Contamination of the benzothiazyl disulfide product with the free 2-mercaptobenzothiazole is very undesirable in the use of the product as a vulcanization accelerator since the free thiol causes premature vulcanization at rubber compounding temperatures. The disulfide is very widely used as an accelerator because of its greater scorch protection, i.e. its lesser tendency to cause premature vulcanization or "scorch" in rubber vulcanizates. In practice a high purity product is desired, containing only a very small amount of the free mercaptan, generally less than 1 to 2 percent.

The requirement of high purity in the precipitated product disulfide has in the past been met by the addition of alkali to the reaction mixture to maintain a high pH, above 8.5–9.0 during substantially the entire chlorine addition. Adequate purity of product could be obtained, but the "over-oxidation" side reactions led to a yield loss of 7 to 10% of the starting 2-mercaptobenzothiazole as water soluble sulfinate and sulfonate salts. These side reactions use 40 to 60% of excess chlorine above stoichiometric requirements for the oxidation to benzothiazyl disulfide and require the aforementioned 0.3 to 1.0 molecular equivalents of alkali to neutralize the acidity formed by the over-oxidation reactions. It is possible to measure the efficiency of the oxidation process by analysis of the reaction slurry for dissolved benzothiazole sulfinates and sulfonates and chlorides, as well as dissolved, unoxidized 2-mercaptobenzothiazole.

In the aforementioned Beber process, under carefully optimized reaction conditions, such as vigorous agitation and fine dispersion of chlorine gas into the aqueous solution of sodium 2-mercaptobenzothiazole solution of about 5–6% concentration, it is necessary to use at least 0.2 moles of a base, e.g. sodium carbonate, to buffer the mixture adequately to prevent contamination of the benzothiazyl disulfide product with free 2-mercaptobenzothiazole. The final slurry contains precipitated benzothiazyl disulfide in about 92% yield; dissolved by-products total about 8%. The sodium chloride produced in the aqueous mixture is equivalent to 32 grams of chlorine consumed per 100 grams of product or 150% of the amount stoichiometrically expected from the simple reaction mechanism proposed hereinabove. If attempts are made to use lower levels of base, e.g. sodium carbonate, lower pH levels occur during the reaction and free mercaptobenzothiazole co-precipitates with and contaminates the product.

In a conventional batch precipitation process as taught in U.S. Pat. Nos. 2,265,344 and 2,468,952, the product quality, as represented by the level of contamination with free mercaptobenzothiazole in the benzothiazyl disulfide produced, can be strongly affected by the concentration of the starting solution of mercaptobenzothiazole. Use of mercaptobenzothiazole solutions greater than about 60 grams per liter leads to products with high mercaptobenzothiazole content (above 2%) even when the most vigorous agitation and thorough chlorine gas dispersion is employed. Use of additional excess alkali, with pH levels up to pH 10, and additional chlorine can lead to some reduction in the amount of contamination with the free mercaptobenzothiazole, but at a high cost in over-oxidation by-products, which are lost in the aqueous filtrate. Yields of less than 90% of benzothiazyl disulfide are then obtained. The necessity for low concentration of reactants requires that large volumes of aqueous solutions must be kept vigorously agitated during the entire time that chlorine is added to the batch, a period of about 2 hours under practical production operations. This requires very large corrosion resistant vessels made of glass, plastics, or high density wood, equipped with powerful agitators, to resist the severe corrosive effects of wet chlorine gas.

In the conventional batch chlorine oxidation process the results are markedly affected by the degree of purity of the 2-mercaptobenzothiazole solution used. In normal large scale commercial operations this solution is ordinarily derived from a relatively crude reaction product of aniline, carbon disulfide and sulfur, as described in U.S. Pat. No. 1,631,871 to Kelly or modifications thereof, by extraction with caustic soda. Various methods are employed to attempt to minimize the carryover of tarry by-product impurities which have some solubility in the sodium mercaptobenzothiazole solution. These residual impurities, often present as 2-3% of the mercaptobenzothiazole, tend to co-precipitate as soft tarry droplets along with the benzothiazyl disulfide and, by occluding the particles of benzothiazyl disulfide, form granular oversized particles known in the art as "sand." This "sand" must be separated from the slurry of benzothiazyl disulfide before further processing because it interferes with milling and screening of the product and causes non-uniform dispersion of benzothiazyl disulfide when compounded into rubber stock as a vulcanization accelerator. The appearance of these sand-like impurities has always been a vexing problem in the production of benzothiazyl disulfide by oxidations of aqueous alkaline solutions of 2-mercaptobenzothiazole and various means have been tried to minimize the contamination. In the Beber process the sodium mercaptobenzothiazole solutions are first purified by precipitation of impurities from the alkaline solution of commercial grade 2-mercaptobenzothiazole of apparent 94-95% purity. In U.S. Pat. Nos. 2,349,599 to Moorhouse, 2,730,528 to Weyker and 3,131,196 to Wood, methods, for purifying solutions of 2-mercaptobenzothiazole as derived from the Kelly process, are suggested; in U.S. Pat. No. 2,830,058 a method for inhibiting the "sand" impurity formation is suggested. In practice none of these methods have proven completely satisfactory. Extra purification steps and more materials are needed and there is a loss in yield of benzothiazyl disulfide based on the starting 2-mercaptobenzothiazole content of the original crude material.

THE INVENTION

We have now found a means whereby all of the above-mentioned drawbacks inherent in prior art procedures for the chlorine oxidation of 2-mercaptobenzothiazole to benzothiazyl disulfide are eliminated or reduced to a surprising degree.

Accordingly it is an object of this invention to provide an improved process for preparing benzothiazyl disulfide by oxidizing sodium mercaptobenzothiazole with chlorine.

An additional object of the invention is to increase the yield of the oxidation process by reducing the losses caused by over-oxidation, which are inherent in prior batchwise processes.

A further object of the invention is to reduce the amount of excess chlorine consumed during the oxidation and thereby to use less alkali.

It is another object of the invention to increase the purity of the benzothiazyl disulfide prepared by the chlorine oxidation process, producing a product with minimum contamination with free mercaptobenzothiazole.

A further object is to utilize sodium mercaptobenzothiazole solutions over a wide range of concentration and purity without the formation of any sand like impurity.

The improved process of this invention comprises the oxidation of 2-mercaptobenzothiazole with chlorine in an aqueous reaction medium, wherein the effective concentration of either reactant is maintained essentially at zero at all times during the reaction and the pH is held between 6 and 9, preferably at about 7. Under these conditions the yield of benzothiazole disulfide is maximum, near 100%, while "over-oxidation" reactions are held to a minimum. The condition of zero reactant concentration at all times is achieved by simultaneously and continuously feeding sodium mercaptobenzothiazole and chlorine gas in such proportions that no free mercaptobenzothiazole can be detected in the reaction mixture and no chlorine gas or hypochlorous acid ion are detected.

Various chemical means may be used to test the reaction mixture for the proper condition at which the process os this invention is operated. A sample of the reaction mixture may be filtered, and the aqueous solution tested for the presence of unoxidized mercaptobenzpthiazole by acidification to produce a haze or precipitate of mercaptobenzothiazole.

The pH of the reaction is measured by any conventional means and alkali added only as necessary to keep it close to neutral at pH 6 to 9.

A convenient and precise method for monitoring and controlling the close stoichiometric ratio of chlorine to sodium mercaptobenzothiazole needed to achieve zero concentration of reactants during the oxidation reaction is provided by measurement of the oxidation-reduction potential, as, for example, a standard calomel reference electrode and an inert metal electrode (commonly platinum).

The oxidation-reduction potential (ORP) of the oxidation reaction is extremely sensitive to changes in the reactant ratio of as little as 1 to 2%, relative. There is a very sharp change of about 300 millivolts in the ORP, corresponding to this change in reactant ratio. The inflection point of this change is found to correspond to the reaction where no unoxidized mercaptobenzothiazole is present in the reaction mixture, and the emf value at this inflection point, as read on an appropriate metering device, will usually be near zero or at some point between $-50$ and $+150$ millivolts. A suitable instrumental control mechanism uses the oxidation-reduction emf value to change the feed rates of the reactants, mercaptobenzothiazole solution and chlorine gas, so as to maintain the reading at a particular emf value corresponding to zero reactant concentration. The actual numerical value of the emf corresponding to the inflection point in the change of oxidation-reduction potential which is used to control the feed rates will, of course, depend on the particular instrumental control system being used, and also somewhat on other factors, such as agitation, placement of gas sparger in the reaction vessel, also upon the presence or absence of impurities found in commercial grade solutions of sodium mercaptobenzothiazole.

pH control and ORP control may be achieved with a variety of instruments available commercially, but pH and ORP are physico-chemical parameters of the oxidation reaction and the process of the invention is not limited to any mechanical means used for their detection and control.

The reactor used for carrying out the process of this invention requires a means for adding separate streams of chlorine gas, aqueous sodium mercaptobenzothiazole solution, and a dilute alkali solution (usually aqueous sodium hydroxide) to a vigorously stirred reaction mixture which is allowed to overflow to a receiving tank. The agitation of the reaction mixture must be such as to overcome the diffusional resistance between the gas and liquid phases of the reaction mass and result in complete absorption of the chlorine with no loss to the atmosphere. In general, a rotating multiple blade agitator producing a high volumetric flow of the reactant mass, along with some shear, is satisfactory. We have found that the best results are obtained when the agitator speed of rotation is such that the tip of the agitator blades have a velocity of at least about 400 ft/min. (80 in./second).

The preferred range of operating conditions for maximum yield and optimum use of chlorine and alkali are those which control the rates of addition of mercaptobenzothiazole solution and chlorine so that the oxidation-reduction potential (ORP) is held at a steady level as near zero as possible, or at the optimum point, which is usually within the range of $-50$ to $+100$ millivolts when measured between an inert platinum electrode and a standard 4N calomel reference electrode. The optimum control point of oxidation-reduction potential is defined as that potential reading (emf) 5 to 25 millivolts above that where the oxidation reaction mixture is found to have no residual unoxidized mercaptobenzothiazole present. The pH of the reaction mixture is kept in the range 6.0 to 8.0 preferably near 7, by the addition of small amounts of alkali. The use of higher ORP levels can cause some colored impurities to be precipitated in the normal, nearly white, precipitated product, while lower potentials can cause a loss of some unoxidized mercapttobenzothiazole in the aqueous mother liquor upon filtration. The process will operate at a pH higher than 8 to 8.5, but at the sacrifice of a small amount of yield loss due to over-oxidation by-products and increased use of alkali and chlorine. At pH levels below about 6-6.5 the control tends to become unsteady and again the quality of the benzothiazyl disulfide is lowered.

The reaction temperature employed may be between about 25° C. and about 65° C. without any significant effect on yield or quality of product. Temperatures in excess of about 75° C. are deleterious and a loss of yield due to side reactions is observed. There is a normal exotherm from the oxidation of mercaptobenzothiazole with chlorine, and this can normally be absorbed by the reaction mixture without provision for cooling. When a 9-10% aqueous sodium mercaptobenzothiazole solution is fed at ambient temperature (20°-30° C.), the reaction mixture will maintain itself at about 50°-55° C.

Since at all times the concentration of each of the reactants in the reaction mixture is very low, close to zero, changes in initial concentration of feed streams have little effect. The sodium mercaptobenzothiazole solutions being used may be at any convenient concentration, with the practical limitation being the concentration of product slurry to provide efficient overflow from the reactor, or pumping to filters for separation from the aqueous mother liquor. The feed solution of sodium mercaptobenzothiazole may have a concentration up to about 50 weight percent, but the preferred range of concentration is from about 2 to 15 percent.

It is not necessary to purify the aqueous sodium mercaptobenzothiazole solution used as the feed stream in the continuous oxidation with chlorine. We have found suitable a wide variety of solutions made by aqueous alkali extraction of the crude mercaptobenzothiazole derived from the aforementioned Kelly process, or by dissolving any commercially acceptable mercaptobenzothiazole product in sufficient aqueous alkali to make a clear solution free of suspended insoluble impurities. In general such solutions can be used for feed stock for the continuous oxidation process so long as there is no suspended particles of tarlike impurities present. Normally the mercaptobenzothiazole content of the solution will have a purity of 97% or greater by conventional assay (titration with standard alkali after precipitation, washing and drying). Solutions of an intermediate quality which, when used in the prior art oxidation processes, produced considerable quantities of by-product tarry agglomerates of a coarse, sand-like nature, when used in the present continuous process, give a fine uniform slurry of benzothiazyl disulfide, free of any sandy agglomerates.

The following examples are offered to further illustrate the novelty and utility of the present invention but not with the intention of unduly limiting the same.

EXAMPLE 1

A 485 gallon corrosion resistant reactor with an overflow at the 350 gallon level is stirred by means of a double impeller turbine blade agitator 22 inches in diameter, tip to tip, rotating at 199 rpm (corresponding to a blade tip velocity of 1146 ft/min. or 229 in./sec.). The reactor is equipped with a gas sparger beneath the agitator for introduction of chlorine gas and means for adding separate aqueous streams of sodium 2-mercaptobenzothiazole and 5% sodium hydroxide solution. A pH electrode assembly and meter is used to monitor the pH of the reaction mixture and a separate oxidation-reduction potential measurement is made by use of a platinum-standard reference cell electrode pair and millivolt meter. To begin operation of the reaction, water is added to the overflow level; then, simultaneously, the flow of sodium mercaptobenzothiazole solution and chlorine is begun. The feed rate of mercaptobenzothiazole solution is fixed at a level corresponding to a desired production rate, e.g. 26 gallons per minute of a solution containing 94 grams per liter of mercaptobenzothiazole. At the beginning, for about 2 to 5 minutes, while steady state operating conditions are being established, the chlorine gas flow is set at about 4.9 lb./min. This corresponds to 1.13 molar ratio based on moles of chlorine per mole of mercaptobenzothiazole, a mercaptobenzothiazole feed rate of 20.4 lb./minute.

The pH of the reaction mixture is observed to fall below 7.0 as read on the pH meter. The pH meter is connected to suitable means to control the rate of addition of 5% sodium hydroxide solution in response to the pH meter reading. The control is set to add just enough dilute sodium hydroxide to counter-act the tendency of pH to drop below a range of 7.2–7.5. The flow of caustic solution is observed to be about 1 to 1.4 gallons per minute.

As the oxidation reaction is begun, the reading of the oxidation-reduction potential (emf) begins to change rapidly in response to slight variations in flow of chlorine or inversely with any slight fluctuation in real 2-mercaptobenzothiazole content in the solution feed stream. The ORP meter is connected through a suitable control valve to adjust the chlorine flow rate in response to the ORP emf reading. An increase in ORP results in a decrease in chlorine flow and, conversely, a decrease in ORP results in an increase in chlorine flow.

As a first approximation in starting up the continuous reaction system, the ORP control point for chlorine flow is set at 0 mv. After several minutes of operation, when the pH and ORP responses are steady within the set ranges, a sample of the reaction mixture is withdrawn from the overflow and tested for dissolved, unoxidized 2-mercaptobenzothiazole by filtration and acidification of the filtrate. A slight precipitate of mercaptobenzothiazole indicates incomplete oxidation. The ORP control point is raised to +10 mv. and thus the chlorine flow control valve opens slightly to feed in additional chlorine. Sampling of the reaction mixture after several minutes of steady operation at the higher oxidation-reduction potential level shows just a faint haze of unoxidized material in the acidification filtrate. The ORP control set point is raised another 10 mv. increment to +20 mv. and this results in a reaction slurry which shows no unoxidized mercaptobenzothiazole in the filtrate upon acidification. (The sensitivity of the test has been found to be 0.01 g/100 ml of mercaptobenzothiazole content). The reaction mixture shows no evidence of chlorine or hypochlorous acid ion when tested with a sensitive starch-potassium iodide paste, nor was any free chlorine found in the air space above the reaction mixture. At this steady state condition, a feed rate of 1223 pounds per hour of real 2-mercaptobenzothiazole solution results in recovery of a slurry of 1195 pounds of benzothiazole disulfide per hour, or 98.3% of theory. The chlorine use is 290 pounds per hour, or 113% of theoretical. Alkali use is equal to 35.9 pounds of sodium hydroxide per hour, 0.12 moles per mole of 2-mercaptobenzothiazole being used. The filtrate, after separation of the product, is analyzed for benzothiazole sulfinate and sulfonate derivatives and it is found to contain a total amount equivalent to 1.7% of the starting mercaptobenzothiazole solution; the chloride content is equal to 112% of theory, based on the 2-mercaptobenzothiazole feed. The dried product is 99.1% pure and contains 0.17% free 2-mercaptobenzothiazole.

To demonstrate the effect of changes in the process operating conditions a series of 30 minute periods is run using different ORP control points for chlorine flow control and at several pH levels. Samples of the reaction slurry are taken under each condition after 20 minutes of steady state operation and the yield and quality of product, as well as reactant usages, is determined by analysis. The data are shown in Table I, Runs A through G.

EXAMPLE 2

Using a different stirred reaction vessel equipped as in Example 1 with pH and ORP measurement meters and control devices, and means for introducing streams of aqueous sodium 2-mercaptobenzothiazole solution, aqueous sodium hydroxide solution and chlorine gas, was used for oxidation of 2-mercaptobenzothiazole to benzothiazyl disulfide. The appropriate steady state condition, with zero concentration of reactants, was achieved in the manner described in Example 1. Sodium 2-mercaptobenzothiazole solution containing 89 g/liter concentration was fed to the reactor at a rate of 17 gallons per minute and the chlorine gas feed rate was first set at 3.0 lb/min., then allowed to vary automatically in response to the ORP measurement. The reaction mixture contained excess unoxidized 2-mercaptobenzothiazole with the ORP control point at 0 to +20 mv. It was necessary to increase the ORP setting to +90 mv. in order to obtain the desired reaction condition. Data from the start-up of this oxidation reaction are presented in Table I, Runs H through J.

Using a different source of sodium 2-mercaptobenzothiazole solution as feed stock in the above reactor, results were obtained as shown in Runs K through M in Table I.

TABLE I

| Run | ORP Setting mv. | pH Control point | Alkali use mole/mole MBT | Precipitation test Unoxidized MBT | Conc. unoxidized MBT | MBTS Product Purity | % Free MBT | % Yield | Yield Loss over-oxidized | Chlorine Use % Theory |
|-----|------|------|------|-------|------|------|------|------|------|------|
| A | +20 | 7.3 | 0.12 | clear | 0.00 | 99.3 | 0.17 | 98.3 | 1.7% | 113 |
| B | +80 | 7.0 | 0.17 | clear | 0.00 | 99.3 | 0.15 | 98.0 | 2.0 | 116 |
| C | +120 | 7.2 | 0.21 | clear | 0.00 | 99.1 | 0.10 | 97.2 | 2.7 | 120 |
| D | −20 | 7.2 | 0.12 | ppt. | 0.12 | 99.0 | .25 | 96.1 | 1.8 | 111 |
| E | −40 | 7.0 | 0.1 | ppt. | 0.31 | 98.7 | .56 | 95.3 | 1.7 | 110 |
| F | +20 | 8.5 | .18 | clear | 0.00 | 99.2 | 0.14 | 97.2 | 2.9 | 118 |
| G | +20 | 6.0 | .07 | clear | 0.00 | 98.0 | 1.10 | 97.5 | 1.8 | 110 |
| H | +60 | 7.2 | | ppt. | 0.16 | | | | | |

TABLE I-continued

| Run | ORP Setting mv. | pH Control point | Alkali use mole/mole MBT | Precipitation test Unoxidized MBT | Conc. unoxidized MBT | MBTS Product Purity | % Free MBT | % Yield | Yield Loss over-oxidized | Chlorine Use % Theory |
| --- | --- | --- | --- | --- | --- | --- | --- | --- | --- | --- |
| I | +80 | 7.2 | 0.11 | haze | 0.03 | | | | | |
| J | +90 | 7.2 | 0.13 | clear | 0.00 | 99.1 | 0.21 | 98.1 | 1.8 | 111 |
| K | 0 | 7.3 | 0.12 | Heavy ppt. | 0.36 | 98.2 | 0.38 | 94.9 | 2.0 | 110 |
| L | +80 | 7.3 | 0.14 | ppt. | 0.10 | | | | | |
| M | +120 | 7.3 | 0.15 | Clear | 0.00 | 98.9 | 0.25 | 97.0 | 2.4 | 117 |

MBT = 2-mercaptobenzothiazole
MBTS = 2,2'-benzothiazyl disulfide

EXAMPLE 3

A batchwise oxidation was conducted in the conventional manner as taught by Beber in U.S. Pat. No. 2,468,952, utilizing a solution of sodium 2-mercaptobenzothiazole made by extraction of the crude product of the process of Kelly, U.S. Pat. No. 1,631,871. The solution is a clear, light yellow color, free of any suspended tar-like impurities, and contains 0.05% of free sodium hydroxide, 49 g/liter 2-mercaptobenzothiazole, and has a purity of 98.0% upon precipitation of a sample with acid and filtering, washing and drying the precipitate.

A corrosion resistant 3 liter vessel was equipped with a high speed agitator and a chlorine dispersion tube extending to the bottom. Two liters of the above solution of the sodium salt of 2-mercaptobenzothiazole, containing 98 g. real (0.586 mole) 2-mercaptobenzothiazole, was added and 17.6 g. (0.166 mole) of sodium carbonate dissolved therein at 30° C. The solution was agitated and chlorine gas introduced at a uniform rate over about 80 minutes, while the concentration of unreacted 2-mercaptobenzothiazole slowly decreased and a cream-white slurry of benzothiazyl disulfide precipitated. When a rapid drop in pH of the resultant slurry was noticed, the chlorine feed was shut off with the reaction mixture at pH 7.3; at this point a sample of slurry, upon filtration and acidification of the filtrate, showed no precipitate of unoxidized 2-mercaptobenzothiazole. The product slurry of benzothiazyl disulfide was poured through a 40 mesh screen and a small quantity of sand-like grains of occluded impure disulfide was recovered. The bulk of the product was filtered, washed free of salts, dried and found to weigh 90.6 grams (93.0% of theory). The impure fraction of the precipitate weighed 1.2 grams. The filtrate (2.6 liters) was analyzed by nitrogen determination for total benzothiazole derivative content and found to contain by-product equivalent to 6.2 grams of 2-mercaptobenzothiazole, representing a 6.5% loss. The chloride content of the aqueous filtrate (determined by "Volhard" analysis) was found to be equal to 30.8 g. (0.434 mole) of chlorine of 143% of the stoichiometric requirements. The product was analyzed and found to have 1.1% free 2-mercaptobenzothiazole content and 96.8% benzothiazyl disulfide content. Its melting range was 166.7°–169.0° C.

EXAMPLE 4

A batchwise oxidation was conducted using the prior art procedure of Example 3, but with the starting solution of sodium salt of 2-mercaptobenzothiazole having a concentration of 89 g. 2-mercaptobenzothiazole per liter. The total real 2-mercaptobenzothiazole in 2 liters of solution was 178 g. (1.06 moles).

After addition of 35.6 g. of sodium carbonate to the solution, chlorine gas was added with vigorous agitation until the pH of the mixture dropped to 7.0–7.2 and no more MBT could be precipitated by acidification of a filtrate sample. The precipitated product recovered included 5.2 grams of oversized agglomerates, 10 to 40 mesh in size, and the remainder after filtering, washing free of salts and drying, weighed 157 g. (88.7% of theory) and contained 6% free 2-mercaptobenzothiazole and 92% benzothiazyl disulfide. This product would be inferior for use as a delayed action vulcanization accelerator.

EXAMPLE 5

A 3 liter glass reactor is equipped for continuous feed of aqueous sodium-mercaptobenzothiazole solution, sodium hydroxide solution and chlorine gas, with an overflow tube for withdrawal of product slurry at the 2 liter level. A pair of electrodes for pH measurement and a separate pair (a platinum and a calomel reference) for measurement of oxidation reduction potential are installed, along with a high speed agitator with a plastic-coated propellor, 2 inches in diameter across the blades, and operated at 1000 RPM (tip velocity = 105 in./sec.).

A small amount of water, about 1 liter, is first added to the reactor in order to contact the pH and "redox" electrode pairs. A feed solution of sodium mercaptobenzothiazole at 25° C. containing 9.14 g. of mercaptobenzothiazole per 100 ml. is fed continuously to the agitated reaction mix while chlorine gas is dispersed therein at the constant rate of 0.29 grams per minute. The redox potential is monitored on a millivolt-meter and the rate of feed of sodium mercaptobenzothiazole solution is varied slightly in response to the reading so as to hold the redox potential at a relatively constant level of +50 mv. ±10 mv.

The reaction mixture, when tested by filtration and acidification of the filtrate, shows no evidence of unreacted 2-mercaptobenzothiazole. A negative test with starch-potassium iodide paste shows no active chlorine or hypochlorite in the aqueous reaction mix or in the vapor space of the reactor. The pH of the reaction mixture is held in the range 7.1 to 7.3 by the addition of 5N sodium hydroxide solution. The reaction temperature is 45° C. After 88 minutes of feed, when 1.12 liters of solution containing 102.5 g. of mercaptobenzothiazole (0.617 mole) has been fed, and 22.0 ml. of 5N caustic used, the three feed streams are cut off and the entire product slurry, both the overflow and the contents of the reactor are filtered to recover the precipitated product, which is washed free of salts and dried. The yield is 102.3 g. of benzothiazyl disulfide of 98.1% purity, or 98% of theoretical. The melting point of the product is 176.2°–177.8° C. and the free mercaptobenzothiazole content is 0.41%. The material balance is confirmed by analysis of the aqueous filtrate which is found to contain soluble products of overoxidation equivalent to 2.0 g. of mercaptobenzothiazole. The chloride content of the filtrate totals 25.5 g. (0.359 moles) or 117% of stoichiometric.

EXAMPLE 6

The equipment of Example 5 is used with the same amount of the solution of sodium mercaptobenzothiazole added to the reaction vessel first at 25° C. and diluted to 2 liters with water before any chlorine is added. Chlorine is then added at about the same rate as in Example 5, and the pH of the vigorously agitated mixture held at pH 8.0 by addition of 5N caustic. The mercaptobenzothiazole content of the mixture is gradually depleted as chlorine is added. The reaction end point is signalled by a very sharp rise in the redox potential after 92 minutes of chlorine feed, the redox potential rising from −200 up to +100 in about 1 minute. The reaction is terminated and the mixture separated as before. The product is recovered by filtration, washing and drying. The yield totals 96.2 g. and the product contains 0.94% free mercaptobenzothiazole. The melting range is 166.7°–168.6° C. The aqueous filtrate contains soluble benzothiazole sulfinate and benzothiazole sulfonate salts equivalent to 6.0 g. of mercaptobenzothiazole. The chloride content is 30.1 g. or equivalent to 142% of stoichiometric requirement for simple oxidation to the disulfide.

EXAMPLE 7

A 55 gal. reactor was filled with 40 gallons sodium mercaptobenzothiazole (9.69 g./100 ml.). The agitator was set at 335 RPM and a Beckman pH combination probe and a Beckman redox combination probe were immersed in the solution. Sodium hydroxide solution, 1.95N, was pumped in at 0.26 gal./min. and vaporized chlorine fed in until the pH was 8.9 and the redox potential was +90 mv. Sodium mercaptobenzothiazole solution (0.69 g./100 ml.) was then pumped in at 25° C. at a rate of 47.5 gal./min. The sodium hydroxide solution and chlorine flow were controlled to maintain the pH between 8.9 and 9.4 and the redox potential between +90 mv. and 150 mv. A slurry of benzothiazyl disulfide at 49° C. was continuously withdrawn at the overflow. After a steady state condition was obtained, benzothiazyl disulfide was produced at a yield of 99.4% having a purity of 96%.

We claim:

1. In a process for preparation of 2,2$^1$-benzothiazyl disulfide by oxidation of 2-mercaptobenzothiazole with chlorine, the improvement which comprises the steps of:

a. simultaneously and continuously introducing below the surface of a vigorously agitated aqueous reaction mixture separate reactant streams of chlorine gas and an aqueous solution of alkali metal salt of 2-mercaptobenzothiazole in approximately stoichiometric proportions, while continuously measuring the oxidation-reduction potential and the pH of said reaction mixture and maintaining the reaction mixture temperature in the range from about 50° C. to 60° C., and b. varying the rate of addition of chlorine gas in response to changes in the measured oxidation-reduction potential as needed to continuously maintain said measured potential at a particular emf corresponding to the emf at zero concentration of the reactants in the reaction mixture, and c. adding alkali metal hydroxide to said reaction mixture in response to changes in the measured pH as needed to continuously maintain said measured pH in the range about pH 6 to 9, and d. removing precipitated 2,2$^1$-benzothiazyl disulfide product from the reaction mixture.

2. The process according to claim 1 wherein said alkali metal salt of 2-mercaptobenzothiazole is the sodium salt and said alkali metal hydroxide is sodium hydroxide.

3. The process according to claim 1 wherein the alkali metal salt solution of 2-mercaptobenzothiazole has a concentration of from about 2 to 15 percent by weight.

4. The process according to claim 1 wherein the pH is maintained in the range 7 to 8.5.

5. The process of claim 1 wherein the emf value is maintained at between −50 to +150 millivolts.

* * * * *